United States Patent [19]

Chu et al.

[11] Patent Number: 5,371,276
[45] Date of Patent: Dec. 6, 1994

[54] RING-OPENING POLYMERIZATION OF CYCLIC ETHERS

[75] Inventors: Shiao-Jung Chu, Hsinchu; Fu-Chen Liu, Nan-Tou Shiann; Ching-Tang Lin, Hsinchu; Huey-Jiuan Yeh, Hsinchu; Fu-Hsi Yu, Hsinchu, all of Taiwan, Prov. of China

[73] Assignee: Industrial Technology Research Institute, Hsinchu, Taiwan, Prov. of China

[21] Appl. No.: 157,960

[22] Filed: Nov. 24, 1993

[51] Int. Cl.$^5$ ............................................. C07C 67/24
[52] U.S. Cl. .................................................. 560/240
[58] Field of Search ....................................... 560/240

[56] References Cited

U.S. PATENT DOCUMENTS

| | | | |
|---|---|---|---|
| 4,680,358 | 7/1987 | Yu | 526/292.9 |
| 4,786,703 | 11/1988 | Starner et al. | 528/63 |
| 4,847,332 | 7/1989 | Yu | 525/398 |
| 4,959,481 | 9/1990 | Axelrod et al. | 548/462 |
| 4,968,746 | 11/1990 | DeRudder et al. | 525/63 |

Primary Examiner—Arthur C. Prescott
Attorney, Agent, or Firm—Darby & Darby

[57] ABSTRACT

A method for preparing ester end-capped polyalkylene ether is disclosed. Cyclic ether monomers are subjected to ring-opening polymerzation at a temperature of 20°–80° C. and a pressure of 0–10 atm in the presence of a solid acid serving as catalyst and a mixture of acid and acid anhydride serving as a promoter. The solid acid is an oxide of group III and group IV elements and has been modified by sulfuric acid, ammonium sulfate or ammonium sulfite.

17 Claims, No Drawings

RING-OPENING POLYMERIZATION OF CYCLIC ETHERS

BACKGROUND

The present invention relates to a method for preparing ester end-capped polyalkylene ether. In particular, it relates to a method for preparing ester end-capped polyalkylene ether by ring-opening polymerization of cyclic ether in the presence of a solid acid of an oxide of group III and group IV elements, which has been modified by sulfuric acid, ammonium sulfate or ammonium sulfite as a catalyst and a mixture of acid and acid anhydride as a promoter.

Ester end-capped polyalkylene ethers are very important intermediates for industrial applications which can be converted to polyether glycols by hydrolysis or alcoholysis. Polyether glycols are used as a starting material for plastic elastomers such as polyurethanes, and spandex fibers. Due to their superelasticity, superior chemical resistance, and air permeability, they have been extensively used in the manufacture of flexible, air ventilating clothes; panty hose; impact resistant motor parts; adhesives; paints; artificial organs; and artificial blood vessels.

Conventional manufacturing process for polyether glycols involves polymerizing cyclic ether into corresponding acid anion end-capped polyethers by the ring-opening process in the presence of a strong liquid acid as the catalyst, followed by subjecting them to hydrolysis or alcoholysis to form hydroxy group end-capped polyether glycols. For example, U.S. Pat. No. 4,510,333 and EP 0167292 A1 disclose a method in which tetrahydrofurans are polymerized into flurosulfonic anion end-capped polyethers by the ring-opening process in the presence of fluorosulfonic acid as a catalyst. U.S. Pat. No. 3,712,430 and Japan Patent No. Sho 45-13940 disclose the same method but fuming sulfuric acid and perchloric acid are respectively used as catalysts instead of flurosuifonic acid. One disadvantage of these methods are that the molecular weight distribution of the resulting polyether is rather broad, the number average molecular weight ranges from 500 to several ten thousands and the molecular weight distribution ($\overline{Mw}/\overline{Mn}$) is much greater than. 2, Another disadvantage of this method is that the liquid acid catalyst used can not be recycled for use because it is very difficult to separate from the product prior hydrolysis or alcoholysis reactions. This leads to the consumption of a large amount of energy. Furthermore, the corrosion of reaction vessels, and the need of sequential treatment of waste acid require a great deal of labour and cost.

U.S. Pat. Nos. 4,153,786 and 4,202,964 and German Patent GB 2025995 disclose a new process which involves carrying out ring-opening polymerization in the presence of a cationic ion exchange resin bearing —$SO_3H$ groups as a catalyst and an acetic anhydride as a precursor. However, since the water content of the catalyst must be strictly limited, the raw material tetrahydrofurans must be predehydrated to contain less than 100 ppm of water. Furthermore, as the cationic ion exchange resin used is normally poor-heat resistant, there are difficulties when a regeneration is desired.

U.S. Pat. Nos. 4,564,671. 4,728,722 and 4,803,299 disclose a process for the preparation of polytetramethyl ether acetate(PTMEA), which uses a bleaching earth catalyst or a zeolite catalyst and acetic anhydride. The disadvantage to this process is that the molecular weight distribution of the resulting PTMEA is relatively broad, and the Mw/Mn is about 3.0.

U.S. Pat. No. 4,568,775, Japan Patent Nos. Sho 63-30931, 63-30930, and laid-open Patent Nos. Sho 61-268787 60-158218 disclose a process for directly producing polyether glycols by using a heteropoly-acid as a catalyst. The process can synthesize polyether glycols in a single step, however, as the heteropoly-acid catalyst is readily soluble, it will remain in and stain the final products, and therefore requires of further treatment of the final product. Furthermore, the yield of this process is rather low, usually less than 10%.

SUMMARY OF THE INVENTION

An object of the present invention is therefore to provide a method for preparing ester end-capped polyalkylene ether in which polymers having a narrower molecular weight distribution can be obtained; the separation of the catalyst can be readily effected, enabling recycling of them and preventing corrosion of the equipment; and the conversion of cylic ether can be raised to above 25%.

It has been found by the inventors that the above object can be attained if cyclic ethers having 3 to 6 carbon atoms are polymerized in the presence of a solid acid of an oxide of group III and group IV elements serving as a catalyst, and a mixture of acid and acid anhydride serving as a promoter, at a temperature of 20°-80° C. and a pressure of 0-10 atm.

According to one aspect of the method of the invention, the raw material, cyclic ethers having 3 to 6 carbon atoms do not require special treatment to remove the water they contain because the solid acid catalyst of the invention has high water endurance.

The present invention can be more fully understood by reading the subsequent detailed description and examples.

DETAILED DESCRIPTION OF THE INVENTION

According to the method of the invention, cyclic ethers having 3 to 6 carbon atoms are suitable for use as raw material. Preferred cyclic ethers are those having the following formula:

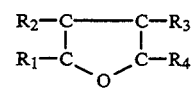

wherein $R_1$, $R_2$, $R_3$ and $R_4$ are alkyl having 1–4 carbon atoms. Tetrahydrofurans are the most preferred cyclic ethers. Normally used tetrahydrofurans which contain about 400 ppm of water, or even industrial-grade tetrahydrofurans which contain about 800 ppm of water, can also be used for monomers of the ring-opening polymerization of the invention.

The solid acid catalysts used according to the present invention are oxides of group III and group IV elements which has been modified by sulfuric acid, ammonium sulfate or ammonium sulfite. Note that the solid acid catalyst should contain 0.01–15, preferably 0.1–10 percent by weight of sulfate ions. Examples of suitable oxides include zirconium dioxide, silicon oxide, titanium dioxide, and ferric oxide . The oxide can be a single oxide or a mixture of two or at least two of the above oxides. The oxide can be prepared by precipitating, coprecipitating or cogrinding methods using salts or oxides of iron, zirconium, silicon, titanium as raw material. The solid acid catalyst are prepared by impregnating the above oxide or mixed oxide with sulfuric acid, ammonium sulfate or ammonium sulfite, followed by fabricating and calcining at a temperature of 350°-800° C., preferably 400°-800° C. with the introduction of air and to form 0.15 cm×0.3 cm pellets. Alternatively, the oxide or the mixed oxide can be ion exchanged with sulfuric, acid, ammonium sulfite or ammonium sulfite, followed by fabricating and calcining at a temperature of 350°-800° C., preferably 400°-800° C. with the introduction of air to form the pellets. The concentration of the sulfuric acid. ammonium sulfate or ammonium sulfite should be 0.1 N-5 N, preferably 0.5 N-3 N.

The ring-opening polymerization according to the invention can be carried out batchwise by using a slurry reactor or continuously by using a fixed-bed reactor If a batchwise slurry reactor is used, the amount of the catalysts should be 5–40 percent by weight, preferably 10–25 percent by weight based on the cyclic ethers. If the amount of the catalyst is less than 5 percent by weight, the time for polymerization is lengthened. On the other hand, if the amount exceeds 40 percent by weight, it is no help to the reaction. The amount of the anhydride should be 2–20 percent by weight , preferably 4–15 percent by weight based on the cyclic ethers. The molar ratio of the acid and acid anhydride should be 10/1 to 1/10, preferably from 8/1 to 1/8. The ring-opening polymerization is carried out at a temperature of 20°-80° C., more preferably between 30°-60° C. for at least 90 minutes. The reaction pressure is preferably from 0–10 atm, more preferably from 1–10 atm. After the completion of the polymerization, the catalyst is filtered and recovered and the formed ester end-capped polyalkylene ether, after separation from unreacted cyclic ether, is sequentially subjected to hydrolysis or alcoholysis to produce polyether glycols. The separated cyclic ethers can be recycled for use. Note that, according to the invention, the recovered catalysts can be reused without further treatment.

If a fixed-bed reactor is used for the ring-opening polymerization, the operation conditions are substantially the same as that of the batchwise slurry reactors. In this case, the catalyst can be reused directly without filtration and separation steps, and the formed ester end-capped polyalkylene ether can be directly collected, thereby rendering the operation more efficiently. The cyclic ethers, acids and acid anhydrides can be fed to the reactor DV using a mixed feed method at a rate of 0.05-5 hr$^{-1}$, preferably 0.1-1 hr$^{-1}$.

The examples which follow illustrate the method according to the invention without implying any limitation. In these examples, tetrahydrofurans(THF) are used as raw material. For batchwise slurry reaction, a 300 ml jacket glass reactor is used and the catalyst is pulverized into particles capable of passing through a 40 to 80 mesh. The reaction conditions and the amount of catalysts are set forth in the examples. For continuous fixed-bed reaction, a one inch glass tube is used as a reactor and 50 ml oxides in the form of 0.15 cm×0.3 cm particles are added as the catalyst. A portion of the collected product is used to determine the conversion of tetrahydrofuran by a HP 5890 gas chromatograph using HP-FFAP(Crosslinked FFAP, 30 m×0.53 mm×1.0 μm glass capillary tube) as separation tube and FID detector. The remaining portion of the product solution is then subjected to vacuum distillation to recover the unreacted tetrahydrofurans. The residual polytetramethylene ether acetate(PTMEA) is then subjected to gel permeation chromatography to measure its number average molecular weight and weight average molecular weight. Conversion of THF and molecular weight distribution of PTMEA are calculated respectively by the following equations.

$$\text{Conversion (mol \%)} = \frac{\text{molar content of THF in the feed} - \text{molar content of THF in the product}}{\text{molar content of THF in the feed}} \times 10\%$$

$$\overline{M_w}/\overline{M_n} = \frac{\text{weight average molecular weight}}{\text{number average molecular weight}} \times 100\%$$

EXAMPLE 1

To 10 liters of distilled water, 2,615 kg of zirconium oxychloride($ZrOCl_2.8H_2O$) was added, stirred to form a solution. 10 percent by weight of ammonia water was dropwise added into the solution until the pH value was adjusted to 10. A white precipitate was formed, filtered, washed and dried for use.

50 g of the white precipitate was then impregnated in 150 ml of 1N sulfuric acid for 1 hours, filtered, dried and extruded into 0.15 cm×0.3 cm pellets. The pellets was then calcined at 550° C. for 5 hours with the introduction of air, about 40 g of catalyst was obtained.

The obtained catalyst was pulverized into 40–80 mesh particles. 15 gram of the pulverized catalyst was placed in a slurry reactor as mentioned above, and 100 g of tetrahydrofuran, 5 g of acetic anhydride and 2 g of acetic acid were added. The reactor was raised to 40° C. and reacted for 5 hours. After the completion of the reaction, the catalyst was removed from the mixture by filtration. The conversion of tetrahydrofuran was analyzed as 37.8%. The obtained polytetramethylene ether acetate had a number average molecular weight of 1210 with a $\overline{M_w}/\overline{M_n}=1.92$ and was colorless.

COMPARATIVE EXAMPLE 1

Sulfonated resin (25 g), THF (100 g), acetic anhydride (5 g), and acetic acid (2 g) was placed in a slurry reactor, and the temperature of the reactor was raised to 40° C. for 3.5 hr. After filtration and separation of the catalyst, the conversion of the tetrahydrofuran was analyzed as 9.2% and colorless polytetramethylene ether acetate with a number average molecular weight of 1310 and $\overline{M_w}/\overline{M_n}=2.0$ was obtained.

EXAMPLE 2

The same procedures as Example 1 were repeated except that 50 g of white precipitate was impregnate in 50 ml of 0.5N sulfuric acid for 30 minutes. The properties of the resultant polymer are listed in Table 1.

EXAMPLE 3

White precipitate (100 g) of Example 1 was impregnated in 200 ml of 5N sulfuric acid for 30 minutes, filtrated, dried, fabricated and then calcined at 650° C. for 4 hours. About 75 g of catalyst was obtained. 50 ml of the catalyst was placed in a fixed-bed tube reactor, and a solution of tetrahydrofuran, acetic anhydride, and acetic acid (molar ratio of 100:8:3) was introduced into the reactor at a rate of 0.5 hr$^{-1}$ by using a high pressure pump and allowed to contact react with the catalyst at 1 atm and 45° C. The product was collected and analyzed to have number average molecular weight of 1130 with a $\overline{M}_w/\overline{M}_n=1.98$, and was colorless. The conversion of the tetrahydrofuran was 39.3%.

EXAMPLE 4

To 10 liters of distilled water 3.63 Kg of tetraisopropoxy-titanium(Ti(OC$_3$H$_7$)$_4$) was added slowly, stirred to form a solution. 10 percent by weight of ammonia water was dropwise added into the solution and the pH value was adjusted to 9. A white precipitate was formed, filtered, washed and dried to titanium hydroxide powder for use.

50 g of the titanium hydroxide powder was impregnated in 200 ml of 1N sulfuric acid for 1 hours, filtered, dried, fabricated and then calcined at 450° C. for 6 hours with the introduction of air. About 39 g of catalyst was obtained.

The obtained catalyst was pulverized. 25 g of the pulverized catalyst of 40–80 mesh was placed in a slurry reactor and allowed to react at 30° C. for 5 hr. The properties of the resultant polymer are listed in Table 1.

EXAMPLE 5

To 10 liters of distilled water, 1.00 Kg of ferric nitrate was added, stirred to form a solution. 10 percent weight of ammonia water was dropwise added in the solution and the pH value was adjusted to 8. Yellow precipitate was formed, filtered, washed and dried to ferric hydroxide powder for use.

50 g of the ferric nitrate powder was impregnated in 200 ml of 0.1N sulfuric acid for 1 hour, filtered, dried and allowed to react by the same conditions as in Example 4. The properties of the resultant polymer are listed in Table 1.

EXAMPLE 6

50 g of the zirconium hydroxide as prepared in Example 1 was impregnated in 150 ml of 5N sulfuric acid for 50 minutes, filtered, fabricated and then calcined at 450° C. for 6 hours with the introduction of air. About 4.5 g of catalyst was obtained.

The obtained catalyst was pulverized. 25 g of the pulverized catalyst of 40–80 mesh was placed in a slurry reactor and 100 g of tetrahydrofuran, 3 g of acetic anhydride and 1 g of acetic acid were added and allowed to react at 40° C. for 3.5 hours. The properties of the resultant polymer are listed in Table 1.

COMPARATIVE EXAMPLE 2

50 g of white powder of zirconium hydroxide of Example 1 was filtered, fabricated and calcined at 550° C. with the introduction of air for 6 hours. 38 g of catalyst was obtained. The catalyst was then pulverized to particles of 40–80 mesh. 25 g of the particles were placed in a slurry reactor and 100 g of tetrahydrofuran, 3 g of acetic anhydride, 1 g of acetic acid were added reacted at 40° C. for 5 hours. The properties of the resultant polymer are listed in Table 1.

COMPARATIVE EXAMPLE 3

50 g of heteropoly-acid catalyst, H$_3$PW$_{12}$O$_{40}$.1.39-H$_2$O, was placed in a slurry reactor and 100 g of tetrahydrofuran was added, and allowed to react at 40° C. for 4 hours. The properties of the resultant polymer are listed in Table 1.

COMPARATIVE EXAMPLE 4

50 g of heteropoly-acid catalyst, H$_4$PSiMo$_{12}$O$_{40}$.1.5-H$_2$O, was placed in a slurry reactor and 100 g of tetrahydrofuran, 5 g of acetic anhydride and 2 g of acetic acid were added, and allowed to react at 40° C. for 3.5 hours. The properties of the resultant polymer are listed in Table 1.

COMPARATIVE EXAMPLE 5

50 g of heteropoly-acid catalyst, H$_4$SiW$_{12}$O$_{40}$.3.45-H$_2$O, was placed in a slurry reactor and 100 g of THF was added, and allowed to react at 40° C. for 4 hours. The properties of the resultant polymer are listed in Table 1.

TABLE 1

| No. | catalyst | amount (g) | reaction time (hr) | THF conversion | color |
|---|---|---|---|---|---|
| Ex. | | | | | |
| 1 | (1N)SO$_4^=$/ZrO$_2$ | 15 | 1.5 | 37.8 | colorless |
| 2 | (0.5N)SO$_4^=$/ZrO$_2$ | 25 | 3.5 | 39.5 | colorless |
| 4 | (1N)SO$_4^=$/TiO$_2$ | 25 | 5 | 25.0 | colorless |
| 5 | (0.1N)SO$_4^=$/Fe$_2$O$_3$ | 25 | 5 | 30.0 | colorless |
| 6. | (5N)SO$_4^=$/ZrO$_2$ | 25 | 3.5 | 36.9 | colorless |
| comp. Ex. | | | | | |
| 1 | Polysiloane-sulfonic resin | 25 | 3.5 | 9.2 | colorless |
| 2 | ZrO$_2$ | 25 | 5 | 7.8 | colorless |
| 3 | H$_3$PW$_{12}$O$_{40}$.1.388H$_2$O | 50 | 4 | 7.2 | light yellow |
| 4 | H$_4$SiMo$_{12}$O$_{40}$.1.5H$_2$O | 50 | 3.5 | 2.8 | light yellow |
| 5. | H$_4$SiW$_{12}$O$_{40}$.3.45H$_2$O | 50 | 4 | 2.9 | light yellow |

It can be seen from Example 3 the above Table 1 that the polytetramethylene ether glycols prepared by the method of the invention have superior ring-opening polymerization activity when compared to the conventional methods which use ion exchange resin bearing —SO$_3$H groups or heteropoly-acid as catalyst. The polyether glycols prepared by the method of the invention have superior quality, are colorless and needless to be further treated, and also have a narrower molecular weight distribution with a $\overline{M}_w/\overline{M}_n$ between 1.8–2.0. The products produced by using heteropoly-acid as catalyst are yellowish in color and therefore need to be subjected to purify treatment.

EXAMPLE 7

The same catalyst as Example 1 was used but the reaction temperature was changed to 30° C. and the reaction time was 3 hours. The conversion of THF was 34.5%. The product, polytetramethylene ether glycol had a number average molecular weight of 1329 with a $\overline{M}_w/\overline{M}_n=1.83$ and was colorless.

EXAMPLE 8

The same catalyst as Example 1 was used but the reaction temperature was changed to 65° C. and the pressure was change to 3 atm. The conversion of THF was 31.6%, The product, polytetramethylene ether glycol had a number average molecular weight of 1030 with a $\overline{M}_w/\overline{M}_n=1.73$ and was colorless.

EXAMPLE 9

The same catalyst as in Example 1 was used, but 10 g of acetic anhydride and 1.0 g of acetic acid were used.

The conversion of THF was 41.3%. The product, polytetramethylene ether glycol had a number average molecular weight of 1305 with a $\overline{M}_w/\overline{M}_n$ of 1.95 and was colorless.

EXAMPLE 10

The same procedures as Example 3 were repeated except that the flow rate of the liquid feed was changed to 2.4 hr$^{-1}$. The conversion of THF was 28.3% and the product, polytetramethylene ether glycol had a number average molecular weight of 1270 with a $\overline{M}_w/\overline{M}_n=1.87$.

EXAMPLE 11

250 g of zirconium hydroxide prepared in Example 1 and 250 g of titanium hydroxide prepared in Example 4 were ground concurrently in a ball mill for 3 hours, dried and impregnated in 0.2N sulfuric acid for 30 minutes. The resulting mixture were then dried by evaporation and fabricated into 0.15 cm×0.3 cm catalyst pellets by using an extruder. The catalyst was then calcined at 800° C. with the introduction of air. 436 g of catalyst was obtained.

The same procedures as Example 3 were repeated except that the flow rate of the liquid feed was changed to 4.5 hr$^{-1}$. The conversion of THF was 27.8%. The obtained polytetramethylene ether glycol had a number average molecular weight of 1639 with a $\overline{M}_w/\overline{M}_n$ of 1.73, and was colorless.

EXAMPLE 12

The same procedures as Example 11 were repeated except that the amount of zirconium hydroxide was changed to 50 g and titanium hydroxide was replaced by 450 g ferric hydroxide. The conversion of the THF was 29.3%. The obtained polytetramethylene ether glycol had a number average molecular weight of 1295 with a $\overline{M}_w/\overline{M}_n$ of 1.91, and was colorless.

What is claimed is:

1. A method for preparing ester end-capped polyalkylene ether, comprising the following steps:
   a) providing a cyclic ether having 3 to 6 carbon atoms;
   b) oligomerically polymerizing said cyclic ether, at a temperature of 20°–80° C. and a pressure of 0–10 atm in the presence of a solid acid serving as a catalyst and a mixture of acid and acid anhydride serving as a promoter, wherein said solid acid is an oxide of group III and group IV elements which has been modified by sulfuric acid, ammonium sulfate or ammonium sulfite; and
   c) separating the resulting ester end-capped polyalkylene ether from the catalyst.

2. The method as claimed in claim 1, wherein the cyclic ether is a tetrahydrofuran derivative of the following formula:

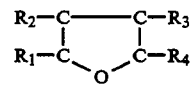

wherein $R_1$, $R_2$, $R_3$ and $R_4$ are alkyl groups of 1 to 4 carbon atoms.

3. The method as claimed in claim 2, wherein said tetrahydrofuran derivative is tetrahydrofuran.

4. The method as claimed in claim 1, wherein the amount of the catalyst is 5–40 percent by weight of the cyclic ether.

5. The method as claimed in claim 1, wherein the amount of the catalyst is 10–25 percent by weight of the cyclic ether.

6. The method as claimed in claim 1, wherein the oxide is a an oxide selected from the group consisting of zirconium dioxide, silicon oxide, titanium dioxide, ferric oxide, and the mixture thereof.

7. The method as claimed in claim 1, wherein the solid acid catalyst contains 0.01–15 percent by weight of sulfate ions.

8. The method as claimed in claim 7, wherein the solid acid catalyst contains 0.1–10 percent by weight of sulfate ions.

9. The method as claimed in claim 1, wherein the solid acid catalyst is prepared by impregnating the oxide with sulfuric acid, ammonium sulfate or ammonium sulfite, followed by calcining at a temperature of 350°–800° C. with the introduction of air.

10. The method as claimed in claim 9, wherein the solid acid catalyst is prepared by impregnating the oxide with 0.1N–0.5N sulfuric acid, followed by calcining at a temperature of 400°–800° C. with the introduction of air.

11. The method as claimed in claim 1, wherein the solid acid is prepared by ion exchanging the oxide, followed by calcining at a temperature of 350°–800° C. with the introduction of air.

12. The method as claimed in claim 1, wherein the acid and acid anhydride are organic acid and its anhydride having 3–5 carbon atoms.

13. The method as claimed in claim 12, wherein the acid is acetic acid and the acid anhydride is acetic anhydride.

14. The method as claimed in claim 1, wherein the amount of the anhydride is 2–20 percent by weight of the cyclic ether and the molar ratio of the anhydride to acid ranges from 10/1 to 1/10.

15. The method as claimed in claim 14, wherein the amount of the anhydride is 4–15 percent by weight of the cyclic ether and the molar ratio ranges from 8/1 to 1/8.

16. The method as claimed in claim 1, wherein the cyclic ether is polymerized at a temperature of 30°–60° C.

17. The method as claimed in claim 1, wherein the cyclic ether is polymerized at a pressure of 1–10 atm.

* * * * *